United States Patent
Schaefer et al.

(10) Patent No.: US 6,566,892 B2
(45) Date of Patent: May 20, 2003

(54) PORTABLE FUEL ANALYZER FOR ANALYZING THE ALCOHOL CONTENT OF A MIXED FUEL

(75) Inventors: Rick Schaefer, Lake Orion, MI (US); Isabelle Desmier, Auburn Hills, MI (US)

(73) Assignee: Siemens VDO Automotive Corporation, Auburn Hills, MI (US)

( * ) Notice: Subject to any disclaimer, the term of this patent is extended or adjusted under 35 U.S.C. 154(b) by 0 days.

(21) Appl. No.: 09/862,081

(22) Filed: May 21, 2001

(65) Prior Publication Data

US 2002/0040593 A1 Apr. 11, 2002

Related U.S. Application Data

(60) Provisional application No. 60/212,693, filed on Jun. 19, 2000.

(51) Int. Cl.[7] .......................... G01R 31/02; G01R 27/26
(52) U.S. Cl. ........................ 324/663; 324/672; 324/601; 324/639
(58) Field of Search ............................... 324/721, 663, 324/672, 601, 608, 683, 674, 685, 639; 422/78, 52; 73/23.2; 205/780

(56) References Cited

U.S. PATENT DOCUMENTS

| | | | | |
|---|---|---|---|---|
| 3,753,092 A | * | 8/1973 | Ludlow et al. ............. 324/663 |
| 3,992,662 A | | 11/1976 | Koepnick et al. ........... 324/442 |
| 4,064,455 A | | 12/1977 | Hopkins et al. ............ 324/663 |
| 4,189,725 A | * | 2/1980 | Rowland .................... 340/636 |
| 4,555,661 A | * | 11/1985 | Benson et al. ............. 324/601 |
| 4,593,357 A | * | 6/1986 | Van Ostrand et al. ....... 364/424 |
| 4,617,278 A | | 10/1986 | Reed ........................... 436/60 |
| 4,635,111 A | * | 1/1987 | Moore ........................ 348/131 |
| 4,675,596 A | * | 6/1987 | Smith ........................ 324/683 |
| 4,757,463 A | * | 7/1988 | Ballou et al. ............... 364/551 |
| 4,818,348 A | * | 4/1989 | Setter ........................ 205/780 |
| 4,869,094 A | * | 9/1989 | Kozuka et al. .............. 73/23.2 |
| 4,989,570 A | | 2/1991 | Kuribara et al. ............ 123/494 |
| 5,005,402 A | | 4/1991 | Pischinger et al. ......... 324/663 |
| 5,025,222 A | * | 6/1991 | Scott et al. ................. 324/639 |
| 5,069,070 A | | 12/1991 | Schmitz ...................... 73/597 |
| 5,124,654 A | | 6/1992 | Scheid ....................... 324/658 |
| 5,134,381 A | * | 7/1992 | Schmitz ...................... 324/685 |
| 5,182,523 A | * | 1/1993 | Ertel et al. .................. 324/663 |
| 5,196,801 A | | 3/1993 | Nogami et al. ............. 324/663 |
| 5,260,665 A | * | 11/1993 | Goldberg et al. ........... 324/636 |
| 5,261,270 A | | 11/1993 | Gonze et al. ............... 73/61.43 |
| 5,337,018 A | | 8/1994 | Yamagishi .................. 324/693 |
| 5,569,922 A | | 10/1996 | Clarke ....................... 250/339.1 |

(List continued on next page.)

FOREIGN PATENT DOCUMENTS

WO    WO 9852073    11/1998

OTHER PUBLICATIONS

PCT International Search Report dated Oct. 30, 2001 PCT/US01/16878.

*Primary Examiner*—N. Le
*Assistant Examiner*—Wasseem H. Hamdan

(57) ABSTRACT

A portable fuel analyzer includes a sensor, a processor and a display. The portable analyzer receives a fuel sample and the display identifies whether the vehicle fuel is tainted. The portable fuel analyzer is linked to an evaluation unit to determine a frequency measurement based upon signals from the sensor in the portable fuel analyzer. The evaluation unit provides a method of comparing the frequency from the vehicle fuel sensor with the frequency from the portable fuel analyzer. If the green LED is illuminated and the portable fuel analyzer indicates a different frequency than the vehicle fuel sensor, the vehicle fuel sensor is defective and should be replaced; If the green LED is illuminated and the portable fuel analyzer indicates the same frequency as the vehicle fuel sensor, a vehicle component other than the vehicle sensor is faulty; and, if the red LED is illuminated, the mixed fuel sample is tainted and a determination about the vehicle fuel sensor cannot be determined.

14 Claims, 2 Drawing Sheets

U.S. PATENT DOCUMENTS

| | | | |
|---|---|---|---|
| 5,594,163 A | | 1/1997 | Suzuki ........................ 73/61.44 |
| 5,807,750 A | * | 9/1998 | Baun et al. .................. 436/164 |
| 5,827,952 A | * | 10/1998 | Mansure et al. ............ 73/61.45 |
| 5,834,638 A | | 11/1998 | Taylor et al. .............. 73/119 A |
| 6,006,022 A | * | 12/1999 | Rhim et al. ..................... 716/1 |
| 6,028,433 A | * | 2/2000 | Cheiky-Zelina et al. .... 324/663 |
| 6,055,468 A | * | 4/2000 | Kaman et al. ................. 701/29 |
| 6,129,895 A | * | 10/2000 | Edmondson .................. 422/78 |
| 6,222,371 B1 | | 4/2001 | Snyder ........................ 324/439 |

\* cited by examiner

PORTABLE FUEL ANALYZER FOR ANALYZING THE ALCOHOL CONTENT OF A MIXED FUEL

The present application claims priority to U.S. Provisional Patent Application Serial No. 60/212,693, filed Jun. 19, 2000.

BACKGROUND OF THE INVENTION

The present invention relates to a portable fuel analyzer, and more particularly to a portable analyzer which identifies whether a vehicle fuel sensor is operating properly.

In some flexible fuel vehicles (FFVs) it has been proposed to use a mixed fuel system for a mixed fuel such as a gasoline/alcohol mixture. In this type of vehicle, a measure is employed in which the fuel injection and ignition timing are controlled in accordance with the mixing ratio of the fuel. A fuel sensor within the vehicle fuel tank measures this ratio. Proper operation of the fuel sensor is thus particularly important to the smooth operation of the engine.

The fuel sensor is typically of a capacitance type that includes a pair of spaced electrodes submerged in the fuel. A signal representative of the capacitance established between the positive and negative electrodes under electrostatic charging is transmitted through lead wires to a separate control circuit where subsequent signal conversion and processing are carried out. The dielectric constant of the fuel is detected by measuring the capacitance established between the electrodes and the mixing ratio of the fuel is derived from the dielectric constant.

In many instances, the fuel sensor may be incorrectly identified when vehicle operation is unsatisfactory. This is undesirable as it is time consuming and expensive to replace the vehicle fuel sensor. It is further desirable to identify whether the quality of the fuel may be the cause of unsatisfactory operation. Accordingly, it is desirable to confirm proper operation of the fuel sensor and fuel quality without actually removing the fuel sensor from the vehicle.

SUMMARY OF THE INVENTION

The portable fuel analyzer according to the present invention includes a funnel to receive a mixed fuel. The funnel includes one or more input ports such that a mixed fuel sample is directed into a container having a sensor. The sensor is a capacitance type sensor which typically includes a pair of spaced electrode plates submerged in the fuel sample within the container. A display which includes a red and a green LED, communicates with the processor to indicate a quality of the fuel mixture.

In use, an operator extracts a mixed fuel sample from a vehicle fuel tank. The fuel sample is pored into funnel such that the fuel sample is collected in the container. The fuel sample forms the dielectric for the sensor. The dielectric constant of the fuel sample is detected by measuring the capacitance established between the electrode plates and the processor determines the alcohol content of the mixed fuel sample.

The processor illuminates either a Red LED or a Green LED if the measured conductance is above or below a predetermined value. The predetermined values are defined to separate an acceptable fuel sample from an unacceptable sample. An operator is thus immediately identified whether the vehicle fuel is tainted.

The portable fuel analyzer is linked to an evaluation unit to determine a frequency measurement based upon signals from the sensor. The frequency measurement is representative of a percentage of alcohol content in the mixed fuel sample. The evaluation unit is linked to a vehicle undergoing service such that the frequency measured by the vehicle fuel sensor can be determined. The evaluation unit compares the frequency from the vehicle fuel sensor with the frequency from the portable fuel analyzer. The following determinations can thus be defined in a rapid and effective manner without the necessity of removing the vehicle fuel sensor from the vehicle:

If the green LED is illuminated and the portable fuel analyzer indicates a different frequency than the vehicle sensor, the vehicle sensor is defective and should be replaced;

If the green LED is illuminated and the portable fuel analyzer indicates the same frequency as the vehicle sensor, another vehicle component is at fault other than the vehicle sensor;

If the red LED is illuminated, the mixed fuel sample is tainted and a determination about the vehicle sensor cannot be determined.

The present invention therefore provides a portable fuel analyzer that receives a fuel sample from a vehicle to determine whether a vehicle fuel sensor is operating properly without actually removing the fuel sensor from the vehicle.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
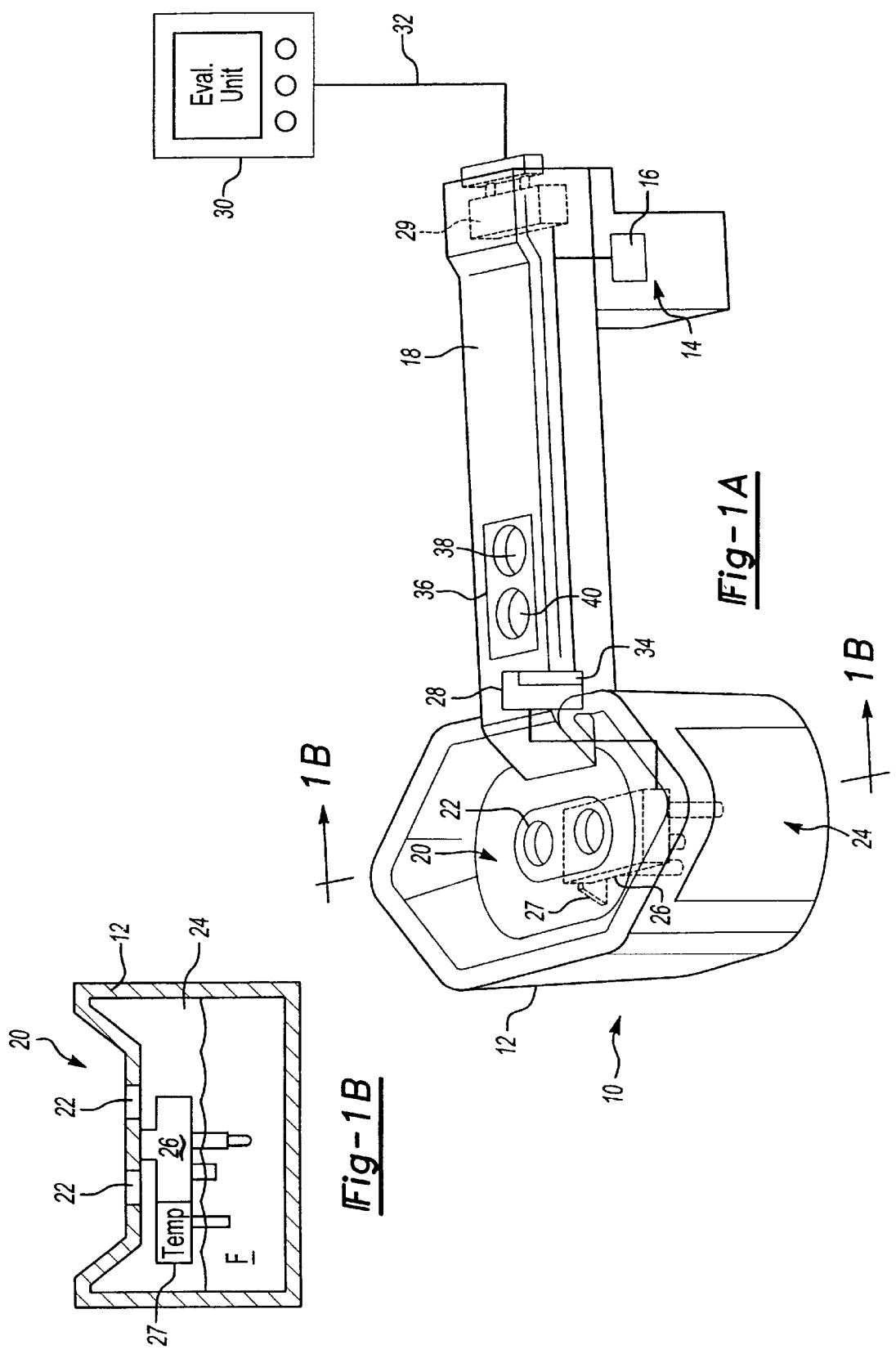
FIG. 1A is a general perspective view of a portable fuel analyzer designed according to the present invention.
FIG. 1B is a sectional view taken along the line of 1B—1B in FIG. 1A.

FIG. 1A illustrates a general perspective view of a portable fuel analyzer 10. The fuel analyzer 10 includes a housing 12 having a power source compartment 14 for a power source 16 such as a battery or the like. A handle 18 is preferably provided such that the analyzer 10 may be conveniently held in a repair-like environment. A portion of the housing 12 is formed as a funnel 20 to receive a mixed fuel sample therein. The funnel 20 includes one or more input ports 22 such that the mixed fuel sample is directed into a container 24 such as a removable fuel bowl.

A sensor (illustrated schematically at 26) is at least partially located within the container 24 such that measurements made thereby are communicated to a processor 28. The sensor 26 is preferably a known capacitance type sensor which typically includes two pairs of spaced electrodes for capacitance and resistance measurements and a thermister for temperature measurement. The electrodes are submerged in the mixed fuel sample F within the container 24 (FIG. 1B). The relative permeability of gasoline differs from that of methanol as well as of ethanol, due to the different molecular dipolarity mainly caused by the different oxygen content. Alcohol and gasoline also show different conductivity.

The relative alcohol content of a fuel is a well defined function of its relative permeability and conductivity. The alcohol content is determined by a capacitance determination—provided with a temperature-dependent correction—by the processor 28. The processor 28 includes logic which enables a suppression of the conductance influence through the analysis of mathematical correlations with a computer or appropriate circuitry in a known manner. The processor 28 thus provides an output value that is linear to the alcohol content despite the non-linear measurement effect.

The housing 12 supports a connector 29 which links the processor 28 to an external evaluation unit (illustrated schematically at 30) through a communication line 32. The evaluation unit is 30 is preferably a digital multimeter or other diagnostic system available in a vehicle service center.

The housing 12 also includes a storage device (illustrated schematically at 34) which communicates with the processor 28. The storage device 34 may include RAM, integrated circuits, or other memory such that the measurements may be temporarily stored in the portable fuel analyzer 10 for later communication to the evaluation unit 30.

A display 36 communicates with the processor 28. The display 36 is provided on the housing 12 to indicate a quality of the fuel mixture. Preferably, the display includes a red and a green Light Emitting Diode (LED) 38, 40. The red LED 38 is illuminated in response to a determination that conductivity as measured by the sensor 26 is above a predetermined value. The green LED 40 is illuminated in response to a determination that conductivity as measured by the sensor 26 is below a predetermined value.

Figure 2:
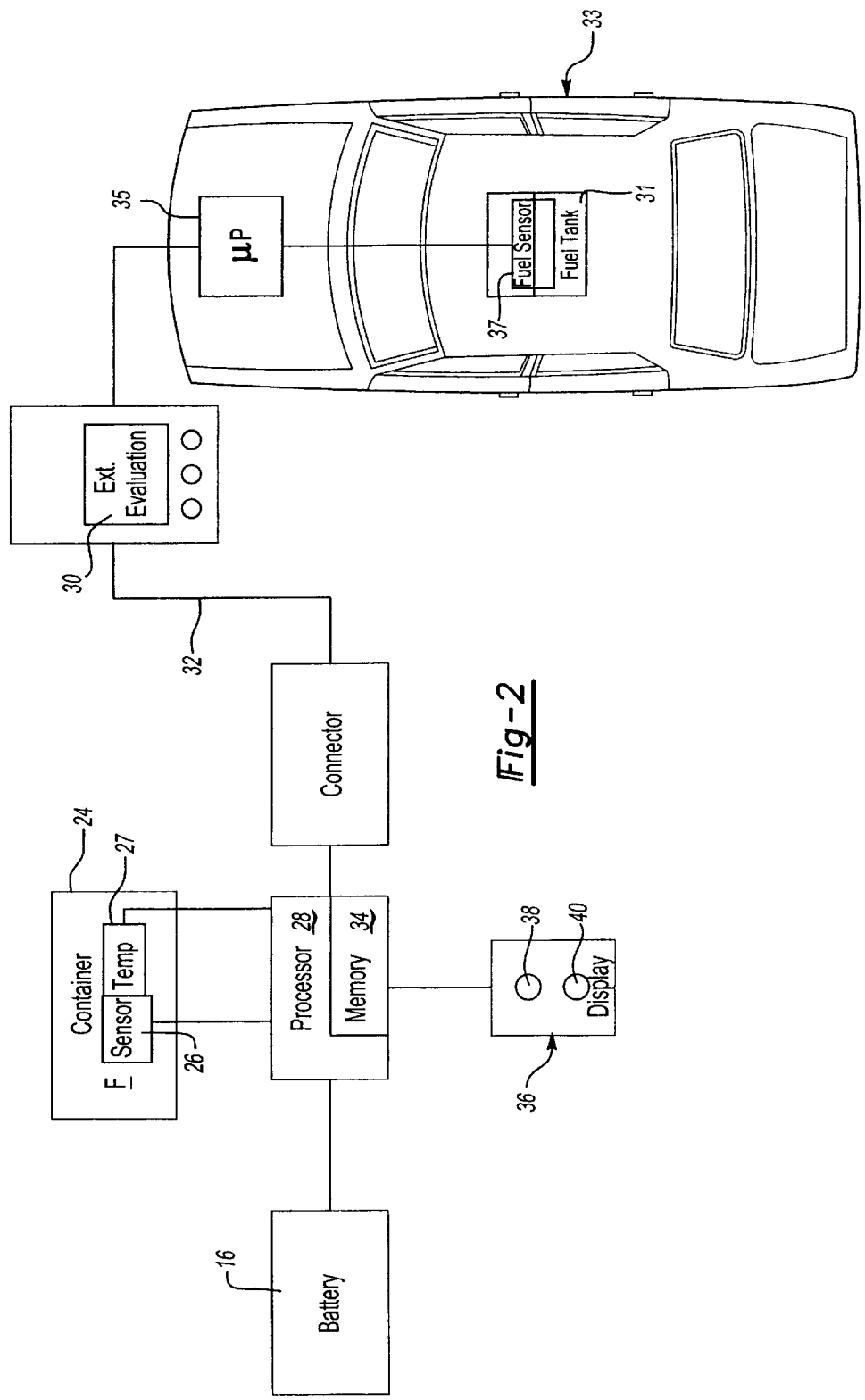
FIG. 2 is a block diagram of the portable fuel analyzer connected to a vehicle.

Referring to FIG. 2, an operator extracts a mixed fuel sample from a fuel tank 31 of a vehicle (illustrated schematically at 33). The fuel sample is pored into the container 24 such that the fuel sample forms the dielectric for the sensor 26 (FIG. 1B). The processor 28 determines the capacitive measured value through the mixed fuel sample F in response to measurements by the sensor 26. Such determinations are known and will not be further described herein.

Since the correlation between relative permittivity and alcohol content within the mixed fuel sample depends heavily on the temperature, it is preferred that the processor 28 relate the capacitive measured value with the value of the fuel temperature from a temperature sensor (illustrated schematically in FIG. 1B at 27) in order to obtain an output quantity that is independent of the temperature and as a measure for the alcohol content. This linking can be performed together with a linearization of the output voltage by the processor 28. Especially preferred is the application of a processor normally used within a vehicle for injection and/or ignition control of the air: fuel mixture.

The processor 28 illuminates either the Red LED 38 or the Green LED 40 if the measured capacitance is above or below a predetermined value. The predetermined values are defined to separate an acceptable fuel sample from an unacceptable sample. In other words, tainted fuel will light the red LED while acceptable fuel will light the green LED. An operator is thus immediately identified that the vehicle fuel is the problem and not a vehicle fuel sensor 37.

The portable fuel analyzer 10 is preferably linked to the evaluation unit 30 to determine a frequency measurement from sensor 26. It should be understood that the memory 34 may temporarily store the measurements such that the analyzer 10 may be connected to the evaluation unit 30 at a later time. The frequency measurement represents a percentage of alcohol content in the mixed fuel sample. In one example, 50 HZ corresponds to 0% ethanol and 100% gasoline while 150 HZ corresponds to 100% ethanol and 0% gasoline. Additionally, the output duty cycle is related to the temperature measurement. The functions are linear for other intermediate mixtures.

The evaluation unit 30 is also linked to a vehicle controller 35 which communicates with a vehicle fuel sensor 37. It should be understood that an engine controller or the like which communicates with the vehicle sensor 37 will benefit from the present invention. The vehicle controller 35 communicates with the vehicle fuel sensor 37 to measure a frequency from the vehicle fuel sensor 37 in a known manner for injection and/or ignition control of the air: fuel mixture. The evaluation unit 30 will then compare the frequency from the vehicle fuel sensor 37 with the frequency from the portable fuel analyzer 10.

The following determinations can thus be defined in a rapid and effective manner without the necessity of removing the vehicle fuel sensor 37 from the vehicle 33:

If the green LED is illuminated and the portable fuel analyzer 10 indicates a different frequency than the vehicle sensor 37, the vehicle sensor 37 is defective and should be replaced;

If the green LED is illuminated and the portable fuel analyzer 10 indicates the same frequency as the vehicle sensor 37, another vehicle component is at fault other than the vehicle sensor 37; and If the red LED is illuminated, the mixed fuel sample F is tainted and a determination about the vehicle sensor 37 cannot be determined.

The foregoing description is exemplary rather than defined by the limitations within. Many modifications and variations of the present invention are possible in light of the above teachings. The preferred embodiments of this invention have been disclosed, however, one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A portable fuel analyzer for a fuel mixture comprising:
   a housing having an opening to a container;
   a sensor communicating with said container such that a mixed fuel sample within said container operates as a dielectric for said sensor;
   a processor communication with said sensor, said processor operable to determine as alcohol content of the mixed fuel sample in response to said sensor;
   a connection for communication between said processor and an evaluation unit which operates to communicate with a vehicle processor;
   a temperature sensor communicating with said container and said processor to sense a temperature of the mixed fuel sample; and
   a display within said housing, said display communicating with said sensor and said processor to indicate a quality of the fuel mixture in response to a predetermined conductivity, wherein said display includes a first and a second indicator, said first indicator activatable in response to a valid fuel mixture quality, and said second indicator activatable in response to an invalid mixed fuel sample quality.

2. The portable fuel analyzer as recited in claim 1, wherein said housing includes a funnel adjacent said opening.

3. The portable fuel analyzer as recited in claim 1, wherein said housing includes a power source.

4. The portable fuel analyzer as recited in claim 1, wherein said housing includes a handle.

5. The portable fuel analyzer as recited in claim 1, wherein said evaluation unit includes a multimeter.

6. The portable fuel analyzer as recited in claim 1, wherein said first indicator activatable in response to said sensor sensing a conductivity below a first predetermined value, and said second indicator activatable in response to said sensor sensing a conductivity above a second predetermined value.

7. The portable fuel analyzer as recited in claim 1, wherein said first and second indicator is a Light Emitting Diode.

8. The portable fuel analyzer as recited in claim 1, wherein said processor comprises an air: fuel mixture processor.

9. The portable fuel analyzer as recited in claim 1, wherein said processor comprises an injection processor.

10. The portable fuel analyzer as recited in claim 1, wherein said processor comprises an ignition processor.

11. A method of analyzing a mixed fuel sample comprising the steps of:
    (1) removing a mixed fuel sample from a vehicle;
    (2) containing the mixed fuel sample in a portable fuel analyzer;
    (3) determining whether the mixed fuel sample is of acceptable quality wherein said display includes a first and a second indicator, said first indicator activatable in response to a valid fuel mixture quality, and said second indicator activatable in response to an invalid mixed fuel sample quality wherein said step (3) further includes:
        3a. measuring a conductivity of the mixed fuel sample;
        3b. activating a first indicator if said conductivity of said step 3a, is below a first predetermined value; and
        3c. activating a second indicator if said conductivity of said step 3a, is above a second predetermined value;
    (4) determining an alcohol content of the mixed fuel sample; and
    (5) comparing the alcohol content determined in said step (4) with an alcohol content measure by a vehicle sensor.

12. A method as recited in claim 11, further including the steps of:
    4a. measuring a frequency indicated by the portable fuel analyzer; and
    4b. comparing the frequency of said step 4b with a frequency measure by a vehicle sensor.

13. A method of analyzing a fuel mixture unit comprising the steps of:
    (1) removing a mixed fuel sample from a vehicle;
    (2) containing the mixed fuel sample in a portable fuel analyzer;
    (3) determining whether the mixed fuel sample is of acceptable quality in response to a conductivity of the mixed fuel sample;
    (4) activating a first indicator if said conductivity of said step (3) is below a first predetermined value;
    (5) activating a second indicator if said conductivity of said step (3) is above a second predetermined value.
    (6) measuring the capacitance of a capacitor sensor formed in which the mixed fuel sample is a dielectric for said capacitor sensor;
    (7) determining an alcohol content of the mixed fuel sample in response to a frequency indicated by the capacitor sensor of said (6); and
    (8) comparing the frequency of said step (7) with a frequency measure by a vehicle sensor.

14. A method as recited in claim 13, wherein said step (7) further includes:
    7a. measuring a temperature of the mixed fuel sample; and
    7b. adjusting said alcohol content of the mixed fuel sample in response to the temperature measured in said step 7a.

* * * * *